United States Patent [19]

Katayama et al.

[11] Patent Number: 5,026,723
[45] Date of Patent: Jun. 25, 1991

[54] MICROBICIDAL/MICROBIOSTATIC COMPOSITION FOR INDUSTRIAL USE

[75] Inventors: Sakae Katayama, Osaka; Yosuke Ito, Ohtsu; Hidenori Hirashima, Osaka, all of Japan

[73] Assignee: Katayama Chemical, Inc., Japan

[21] Appl. No.: 339,124

[22] Filed: Apr. 14, 1989

[30] Foreign Application Priority Data

Apr. 18, 1988 [JP] Japan .................................. 63-96523

[51] Int. Cl.$^5$ ..................... A01N 37/00; A01N 37/02; A01N 43/26
[52] U.S. Cl. ................................... 514/441; 162/161; 210/764; 514/529; 514/547
[58] Field of Search ...................... 514/441, 547, 529; 162/161; 210/764

[56] References Cited

U.S. PATENT DOCUMENTS 4,647,577  3/1987  Umekawa et al. .................. 514/547

FOREIGN PATENT DOCUMENTS 0036055  9/1981  European Pat. Off. ............ 514/547

OTHER PUBLICATIONS

Buckley, C.A. vol. 96 (1982) 96:68312r.

Primary Examiner—Allen J. Robinson
Attorney, Agent, or Firm—Bryan, Cave, McPheeters & McRoberts

[57] ABSTRACT

A microbicidal/microbistatic synergistic composition for industrial use comprising a specific nitrobromopropane derivative and 4,5-dichloro-1,2-dithiol-3-one and an industrial method of killing or inhibiting the growth of microorganisms using the same compounds, which are useful of microbicidal/microbistatic treatment in various industrial media.

13 Claims, 4 Drawing Sheets

MICROBICIDAL/MICROBIOSTATIC COMPOSITION FOR INDUSTRIAL USE

BACKGROUND OF THE INVENTION

1. Field of the Invention

The present invention relates to a microbicidal/microbistatic composition for industrial use and its use. More particularly, it relates to a microbicidal/microbistatic composition for industrial use and a method of killing or inhibiting the growth of microorganisms, which can be used for microbicidal/microbistatic treatment of papermaking process water in paper and pulp industry, cooling water or washing water for various industries, heavy oil sludges, cutting oils, textile oils, paints, antifouling coatings, paper coating liquids, latices, sizings or the like.

2. Description of the Prior Art

It has been known that in papermaking process water of paper and pulp industry and cooling water of various industries, slimes are generated due to the growth of bacteria and/or fungi and results in such problems as lowering of the quality of products and the efficiency of production. Further, in many industrial products, for example heavy oil sludges, cutting oils, textile oils, paints, various latices, and sizings, putrefaction and contamination occur due to the growth of bacteria and fungi to reduce their value.

Thus, many microbicidal agents have been used in order to prevent the problems induced with such microorganisms. Formerly, organomercury compounds, chlorinated phenol compounds and the like were used for this purpose. But, these compounds generally show strong toxicity to human body, fishes and shellfishes, and cause environmental contamination. Therefore, their use comes to be regulated. Recently, relatively low toxic compounds such as described below have been generally used as microbicidal compounds for industrial use, namely, organonitrogene-sulfur compounds such as methylene bisthiocyanate, 1,2-benzoisothiazoline-3-one and 5-chloro-2-methyl-4-isothiazoline-3-one; organobromine compounds such as 2,2-dibromo-2-nitroethanol, 2,2-dibromo-3-nitrilopropionamide, 1,2-bis(bromoacetoxy)ethane, 1,4-bis(bromoacetoxy)-2-butene and bistribromomethyl sulfone and the like; and organosulfur compounds such as 4,5-dichloro-1,2-dithiol-3-one.

Such known compounds show different microbicidal spectra and effects and are used corresponding to their working objects. For example, 4,5-dichloro-1,2-dithiol-3-one, 2,2-dibromo-2-nitroethanol, 2,2-dibromo-3-nitrilopropionamide, bistribromomethylsulfone and the like exhibit an action that their addition even in a small amount remarkably decreases the number of viable bacteria, which is referred to as "microbicidal action" hereafter, but they are not potent in the action of inhibiting the growth of viable bacteria for a long period of time, which is referred to as "antimicrobial (microbistatic) action". Further, methylene bisthiocyanate, 1,2-bis (bromoacetoxy)ethane, 1,4-bis(bromoacetoxy)-2-butene and the like have a microbistatic action, but are required to maintain in a high concentration for a long period in order to exert their microbicidal action.

Therefore, the above mentioned ingredients are often used in a manner of their appropriate combination and this can sometimes develop a synergistic effect. But the effective combinations are limited in number. In addition, it is also known that when a composition containing a single ingredient is continuously used, resistant bacteria occur to decrease the effect of the composition.

Further, the temperature of industrial process water or industrial products to be subjected to a microbicidal/microbistatic treatment will greatly vary depending on seasons or working factors. For example, the temperature of papermaking process water is about 40° C. in summer but drops into 15° C. or lower in winter. Such temperature drop is known to be generally a factor remarkably reducing microbicidal/microbistatic effects of bactericidal compounds.

The present invention was made under the above circumstances, and its purpose is to provide a composition which can exhibit sufficient microbicidal/microbistatic action in a smaller amount and can maintain its effects even at lower temperature.

Nitrobromopropane derivatives of the formula (I) as mentioned below are known from the disclosures in Japanese Published Examined Patent Application No. 16460/1968, EPA No. 36055 and EPA No. 34684 to have solely a microbicidal activity but they are not known to exhibit a synergistic effect by combination use with other agent(s) and maintain this effect even at low temperature.

On the other hand, 4,5-dichloro-1,2-dithiol-3-one as disclosed in for example U.S. Pat. Nos. 4,334,957 and 4,647,577, etc., is known to have a microbicidal effect by itself and also exert a synergistic effect by the specific combination use with some agents. However, the combination use of the above compound and the nitrobromopropane derivatives of the formula (I) is not known.

SUMMARY OF THE INVENTION

According to the present invention, there is provided a microbicidal/microbistatic composition for industrial use comprising as active ingredients a nitrobromopropane derivative of the formula (I):

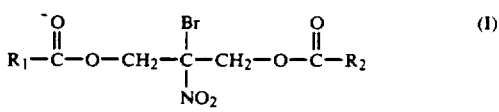

wherein $R_1$ and $R_2$ are the same and are a hydrogen atom or a methyl group, and 4,5-dichloro-1,2-dithiol-3-one. Further, there is provided a method of killing or inhibiting the growth of microorganisms by using the above active ingredients in an industrial medium.

DETAILED DESCRIPTION OF THE PREFERRED EMBODIMENT

Figure 1:
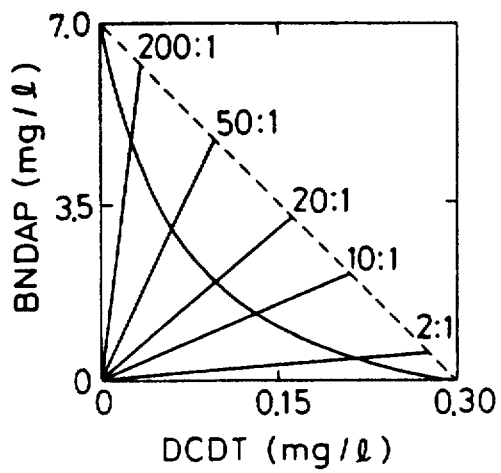
FIGS. 1 to 4 and 6 to 13 are graphs showing synergistic effects of microbicidal/microbistatic compositions of the present invention.

The compounds of the formula (I) in the present invention include 2-bromo-2-nitro-1,3-diacetyloxypropane (referred to as BNDAP hereafter) and 2-bromo-2-nitro-1,3-diformyloxypropane (referred to as BNDFP hereafter). The ratio of the compound of the formula (I) and 4,5-dichloro-1,2-dithiol-3-one (referred to as DCDT hereafter) is suitably 200:1 to 1:10 (by weight), preferably 100:1 to 1:5 and more preferably 50:1 to 1:2, from the viewpoint of microbicidally synergistic effect. On the other hand, from the viewpoint of microbistatically synergistic effect, it is suitably 100:1 to 1:5.

The two kinds of active ingredients in the present invention are usually used as an one-pack preparation to industrial media requiring microbicidal/microbistatic treatment. However they may be separately (as they are or separate preparations) added to the industrial media. Generally the one-pack preparation is preferable.

In order to prepare the one-pack liquid preparation, organic solvents and dispersing agents are generally used. When it is used in an industrial medium of water system such as papermaking process water, industrial cooling water and the like, the preparation may be preferably prepared by use of hydrophilic organic solvents and dispersing agents from a viewpoint of solubility or dispersibility in water of the ingredients. Examples of the hydrophilic organic solvents are anides such as dimethylformamide; glycols such as ethylene glycol, propylene glycol, diethylene glycol and dipropylene glycol; glycol ethers such as methyl cellosolve, phenylcellosolve, diethylene glycol monomethyl ether, dipropylene glycol monomethyl ether and tripropylene glycol monomethyl ether; alcohols containing up to 8 carbon atoms such as methanol, ethanol, propanol, butanol and octanol; and esters such as methyl acetate, ethyl acetate, 3-methoxybutyl acetate, 2-ethoxymethyl acetate, 2-ethoxyethyl acetate and propylene carbonate. The hydrophilic organic solvents may be used singly or in mixture thereof and also may contain a small amount of water.

It is preferable from the viewpoint of storage stability to use dimethylformamide or esters such as methyl acetate, ethyl acetate, propyl acetate, 3-methoxybutyl acetate, 2-ethoxymethyl acetate, 2-ethoxy ethyl acetate and propylene carbonate and it is more preferable to use dimethylformamide, propylene carbonate or 3-methoxybutyl acetate.

Examples of the dispersing agents are cationic, anionic, nonionic and amphoteric surfactants, nonionic surfactants being preferred because of stability of the preparation. Specifically, the nonionic surfactants include higher alcohol ethylene oxide (EO) adducts, alkyl-phenol-EO adducts, fatty acid-EO adducts, fatty acid polyhydric alcohol ester-EO adducts, higher alkylamine-EO adducts, fatty acid amide-EO adducts, fat-EO adducts, propylene oxide (PO)-EO copolymers, alkylamine PO-EO copolymer adducts, fatty acid glycerol esters, fatty acid pentaerythritol esters, fatty acid sorbitol esters, fatty acid sorbitan esters, fatty acid sucrose esters, polyhydric alcohol alkyl esters and alkylolamides.

The one-pack liquid preparation preferably comprises 1 to 50 parts by weight of a total quantity of the active ingredients and at least 0.01 parts by weight of the dispersing agent per part of the active ingredients, the remainder being the hydrophilic organic solvent.

To the medium of an oil system such as heavy oil sludge, cutting oil or oily paint, the preparation may preferably be added in the form of a one-pack liquid preparation using a hydrophobic organic solvent, e.g., a hydrocarbon solvent such as kerosene, heavy oil or spindle oil, and optionally containing an appropriate surfactant.

To the medium in which the active ingredients of the invention can be directly dissolved or dispersed, the active ingredients may be added directly or in the form of a one-pack powdery preparation which is diluted with solid diluents (e.g., kaolin, clay, bentonite or carboxymethylcellulose) and optionally contains various surfactants. The powdery preparation may be prepared by blending the active ingredients and solid diluent without solvents, depending on the combination of the active ingredients.

A suitable addition amount of the microbicidal/microbistatic composition of the invention depends on the condition of the industrial medium and the object. In particular, to papermaking process water or industrial cooling water, the addition of about 0.05 to 200 mg/l as a total active ingredients concentration in the water will be sufficient for inhibiting the growth of microbes (microbistatic effect) and the addition of 0.5 to 50 mg/l will achieve a microbicidal effect.

In the method according to the present invention, the use of the above mentioned one-pack preparation is convenient. However, separate preparations containing each of the active ingredients may be used upon circumstances.

MICROBICIDAL EFFECT

In the combination of BNDAP and DCDT, or BNDFP and DCDT as active ingredients, the minimum concentration (mg/l) of the ingredients required to decrease the initial number of $10^6$ or more/ml of viable bacteria, *Pseudomonas aeruginosa* or *Staphylococcus aureus*, to $10^3$ or less/ml (with microbicidal effect of 99.9% or more) was determined.

The measuring method of the minimum concentration is as follows.

A bouillon broth was inoculated with the bacterial and preincubated. The obtained culture was added to a sterilized physiological saline so that the number of viable bacteria in the mixture becomes $10^6$ or more/ml. The above ingredients was added to the resultant and shaken for 1 hour at 37° C. The number of surviving bacteria was measured, to determine the minimum concentration required.

Figure 2:
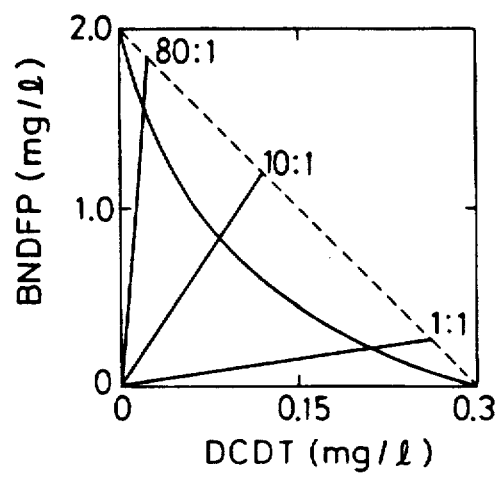
Figure 3:
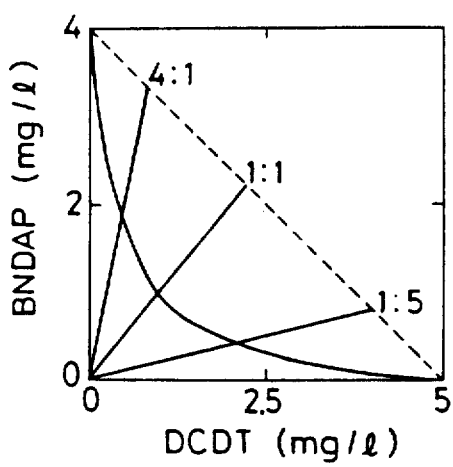
Figure 4:
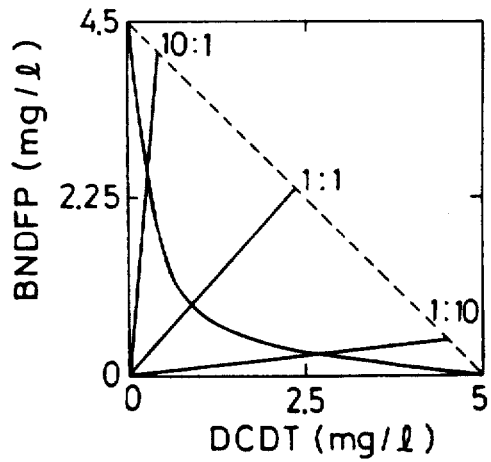

The results on *Pseudomonas aeruginosa* are shown in FIGS. 1 and 2, and those on Staphylococcus aureus are shown in FIGS. 3 and 4.

MICROBISTATIC EFFECT

(1) Evaluation method

A synergistic effect of the combination of the two kinds of ingredients was examined in accordance with the two-dimensional dilution method. Each of the two ingredients was diluted to a predetermined concentration, and a predetermined amount of the resultant was added to a bouillon broth. The broth was inoculated with a microorganism and incubated under a constant condition. The concentration of the ingredients at which no growth of the microorganism was observed was defined as the minimum inhibitory concentration according to the two-dimensional dilution method (hereinafter abbreviated to TDMIC).

Figure 5:
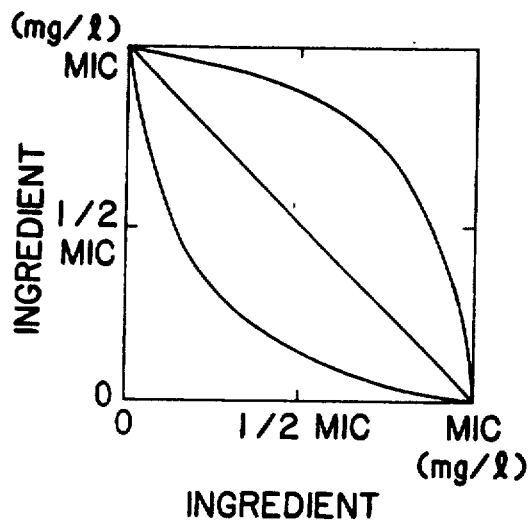
FIG. 5 is a graph explaining a criterion of synergistic effect.

FIG. 5 is a sample of the graph wherein the minimum inhibitory concentrations (MIC. mg/l) of the respective ingredients used alone are expressed by an equal length on the vertical and horizontal axes. In this Figure, the area above the curve, i.e., the TDMIC curve shows the growth inhibition area and the area below the curve is the growth area. A curve positioned over the diagonal line means an antagonistic effect and a curve positioned below the diagonal line expresses a synergistic effect.

(2) Synergistic effect against bacteria

The synergistic effect of BNDAP and DCDP, or BNDFP and DCDP was examined against *Pseudomonas aeruginosa* of typical Gram-negative bacteria which was separated from a slime. The bacteria was preincubated overnight. A bouillon broth was inoculated with a predetermined amount of the resultant culture, and shaken for 24 hours at 37° C. The concentration of the ingredients at which no turbidity of the broth was observed was determined.

Figure 6:
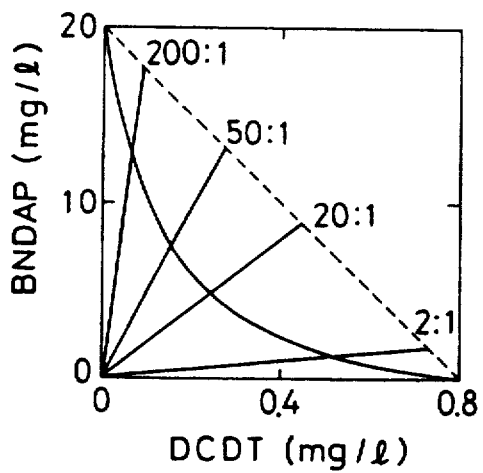
Figure 7:
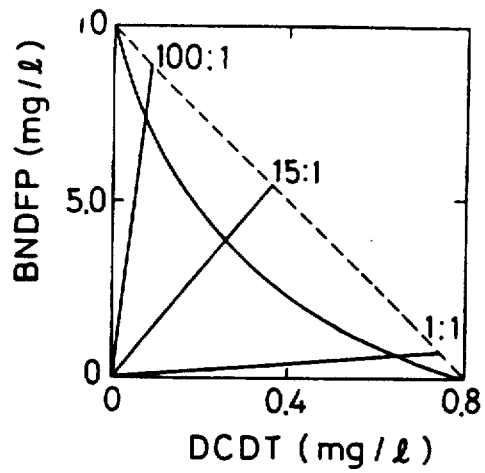

The results are shown in FIGS. 6 and 7.

(3) Synergistic effect against fungi

Figure 8:
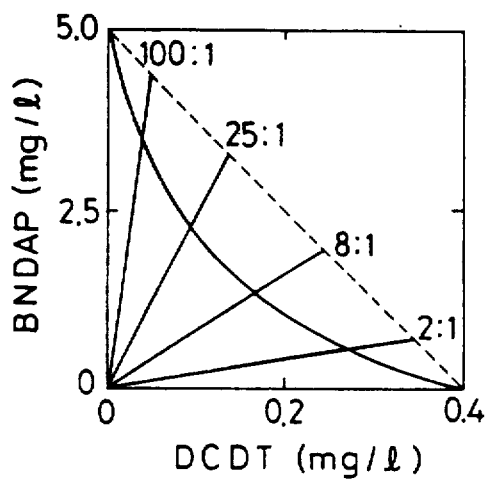
Figure 9:
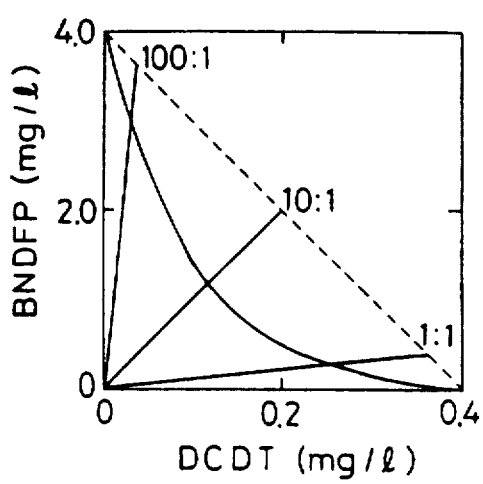
Figure 10:
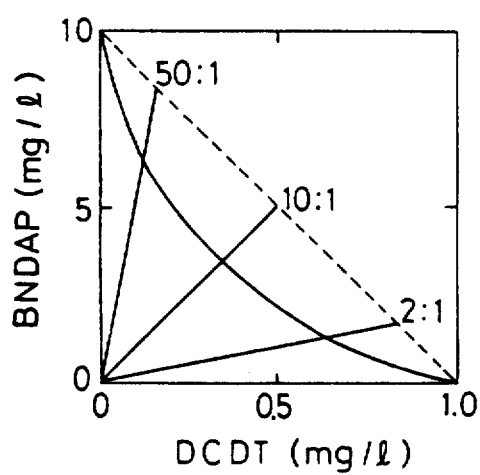
Figure 11:
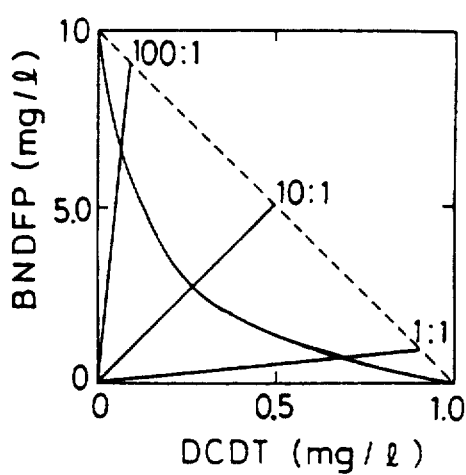

The synergistic effect of the ingredients was examined against *Aspergillus niger* and *Gliocladium virens* which belong to fungi and often occur in wet pulp, starch glue, and coating color. From the strain which was beforehand slant-cultured using Czapek medium, one loopful of the spores was taken and suspended in sterilized water. A Czapek broth was inoculated with a predetermined amount of the suspension and shaken for 7 days at 27° C. The concentration of the ingredient at which no growth of the mycelia was observed was determined. The results on *Aspergillus niger* are shown in FIGS. 8 and 9, and the results on *Gliocladium virens* are shown in FIGS. 10 and 11.

(4) Synergistic effect against yeast

The synergistic effect against a typical yeast, *Rhodotorula rubula* which is often found in starch liquid and coating color liquid was examined.

Figure 12:
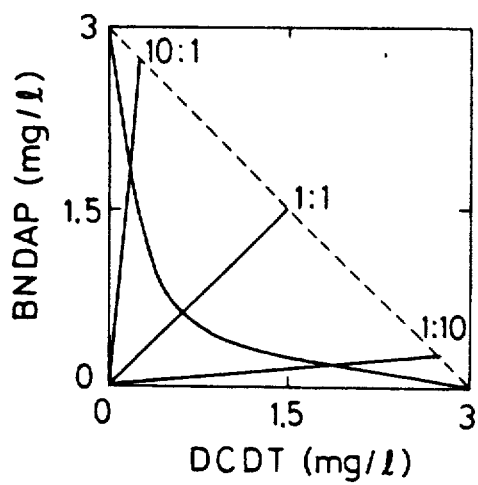
Figure 13:
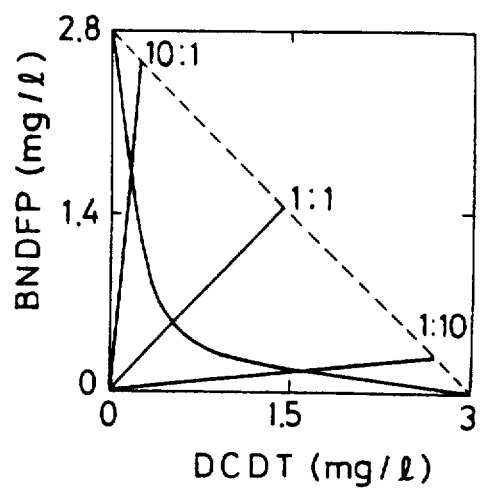

Using YM broth, the yeast was preincubated overnight. With a predetermined amount of the resultant culture solution, a YM broth was inoculated and incubated under shaking for 24 hours at 30° C. The concentration of the ingredient at which no turbidity of the medium was observed was determined. The results are shown in FIGS. 12 and 13.

MICROBICIDAL EFFECT IN WHITE WATER OF PAPERMAKING PROCESS

In a certain paper mill, white water was sampled from a papermaking machine for fine paper (neutral paper). The white water had a pH of 7.4 and contained 8 ppm of $SO_3^{2-}$ and viable microbes mainly consisting of Flavobacterium, Micrococcus, Pseudomonas and Bacillus species. The above ingredients were added to the white water. The resulting white water was shaken for 60 minutes at 37° C. and the number of viable bacteria was determined. The results are shown in Table 1.

TABLE 1

|  | Ingredient | Concentration of ingredient (mg/l) | Number of viable bacteria per ml |
|---|---|---|---|
|  | Not added | 0 | $1.5 \times 10^7$ |
| Comparative Example | BNDAP | 7.5 | $5.6 \times 10^6$ |
|  |  | 15 | $9.2 \times 10^5$ |
|  | BNDFP | 7.5 | $4.5 \times 10^6$ |
|  |  | 15 | $8.1 \times 10^5$ |
|  | DCDT | 7.5 | $8.3 \times 10^6$ |
|  |  | 15 | $6.1 \times 10^6$ |
| Example | BNDAP + DCDT (1:1) | 7.5 | $8.7 \times 10^5$ |
|  |  | 15 | $3.1 \times 10^5$ |
|  | BNDAP + DCDT (4:1) | 7.5 | $6.5 + 10^4$ |
|  |  | 15 | $9.5 \times 10^3$ |
|  | BNDAP + DCDT (19:1) | 7.5 | $7.1 \times 10^5$ |
|  |  | 15 | $4.8 \times 10^4$ |
|  | BNDFP + DCDT (1:1) | 7.5 | $6.1 \times 10^5$ |
|  |  | 15 | $9.7 \times 10^4$ |
|  | BNDFP + DCDT (4:1) | 7.5 | $5.5 \times 10^4$ |
|  |  | 15 | $8.1 \times 10^3$ |
|  | BNDFP + DCDT (19:1) | 7.5 | $3.9 \times 10^5$ |
|  |  | 15 | $2.3 \times 10^4$ |
| Comp. Ex. | DBNE* + DCDT (1:1) | 7.5 | $9.7 \times 10^6$ |
|  |  | 15 | $8.1 \times 10^6$ |

*DBNE means 2,2-dibromo-2-nitro-1-ethanol.

CONSIDERATION

As seen clearly from the results, any of the single ingredients and the combination of DBNE+DCDT only slightly decrease the number of viable bacteria and therefore they are not considered to have a microbicidal effects. However, the combinations of BNDAP+DCDT, and BNDFP+DCDT show very great synergistic effects in their microbicidal power.

INFLUENCE OF TEMPERATURE ON MICROBICIDAL EFFECT IN WHITE WATER OF PAPERMAKING PROCESS

In a paper mill, white water was sampled from a papermaking machine for fine paper (neutral paper). The white water had a pH of 7.0 and contained 0 ppm of $SO_3^{2-}$ and viable microbes mainly consisting of Pseudomonas, Bacillus, Alcaligenes and Klebsiella species. The above ingredients were added to the white water. The resulting white water was shaken for 60 minutes at 15° C. or 35° C. and the number of viable bacteria was determined. The results are shown in Table 2.

TABLE 2

|  | Ingredient | Concentration of ingredient (mg/l) | Number of viable bacteria per ml | |
|---|---|---|---|---|
|  |  |  | 35° C. | 15° C. |
|  | Not added | 0 | $3.5 \times 10^7$ | $2.7 \times 10^7$ |
| Comparative Example | BNDAP | 10 | $9.8 \times 10^6$ | $1.5 \times 10^7$ |
|  |  | 20 | $6.8 \times 10^6$ | $8.3 \times 10^6$ |
|  | BNDFP | 10 | $7.9 \times 10^6$ | $8.7 \times 10^6$ |
|  |  | 20 | $5.1 \times 10^6$ | $6.5 \times 10^6$ |
|  | DCDT | 10 | $7.3 \times 10^6$ | $9.1 \times 10^6$ |
|  |  | 20 | $4.6 \times 10^6$ | $8.6 \times 10^6$ |
| Example | BNDAP + DCDT (5:1) | 10 | $4.9 \times 10^4$ | $7.5 \times 10^4$ |
|  |  | 20 | $6.3 \times 10^3$ | $9.3 \times 10^3$ |
|  | BNDFP + DCDT (5:1) | 10 | $3.0 \times 10^4$ | $2.2 \times 10^4$ |
|  |  | 20 | $4.3 \times 10^3$ | $5.1 \times 10^3$ |
| Comparative example | DBNE[1] + DCD (5:1) | 10 | $1.3 \times 10^6$ | $9.0 \times 10^6$ |
|  |  | 20 | $5.1 \times 10^5$ | $7.9 \times 10^6$ |
|  | BBAE[2] + DCDT (5:1) | 10 | $3.0 \times 10^5$ | $9.1 \times 10^6$ |
|  |  | 20 | $9.8 \times 10^4$ | $8.1 \times 10^6$ |
|  | BTBMS[3] + DCDT (2:1) | 10 | $9.7 \times 10^4$ | $3.3 \times 10^6$ |
|  |  | 20 | $1.9 \times 10^4$ | $9.1 \times 10^5$ |
|  | MBCT[4] + DBNPA[5] | 10 | $8.9 \times 10^4$ | $7.9 \times 10^6$ |

TABLE 2-continued

| Ingredient | Concentration of ingredient (mg/l) | Number of viable bacteria per ml | |
|---|---|---|---|
| | | 35° C. | 15° C. |
| (1:2) | 20 | $2.1 \times 10^4$ | $5.3 \times 10^6$ |
| MIT[6] + BBAB[7] | 10 | $7.7 \times 10^5$ | $8.7 \times 10^6$ |
| (1:3) | 20 | $6.9 \times 10^4$ | $5.1 \times 10^6$ |

[1]DBNE: 2,2-Dibromo-2-nitro-1-ethanol
[2]BBAE: Bisbromoacetoxyethane
[3]BTBMS: Bistribromomethylsulfone
[4]MBTC: Methylene bisthiocyanate
[5]DBNPA: 2,2-Dibromo-3-nitrilopropionamide
[6]MIT: 5-Chloro-2-methyl-4-isothiazoline-3-one
[7]BBAB: Bisbromoacetoxy-2-butene

CONSIDERATION

As seen from the results, single ingredients only slightly decreases the number of viable bacteria and therefore they are not considered to have a microbicidal effects which can prevent troubles resulted from microorganisms.

The combinations of BBAE+DCDT, BTBMS+DCDT, MBTC+DBNPA and MIT+BBAB each exhibited a synergistic effect in their microbicidal effect at 35° C. But when the temperature dropped into 15° C., their microbicidal effect greatly decreased and the synergistic effects shown at 35° C. came to disappear.

On the other hand, the combinations of BNDAP+DCDT and BNDFP+DCDT were observed to have very great synergistic effect. Further, the effect was maintained even if the temperature dropped from 35° C. to 15° C. Thus the above combinations are considered to be very useful as microbicidal agents.

STORAGE STABILITY OF THE INGREDIENTS IN ONE-PACK LIQUID PREPARATION

One-pack liquid preparations were prepared by dissolving BNDAP+DCDT or BNDFP+DCDT in various organic solvents with percentage by weight described in Table 3.

After they were stood for leave in a thermostatic chamber for 30 days at 50° C., the residual amount of each the ingredients was determined with high-pressure liquid chromatography(HPLC) and then the percentage of their residual quantity was calculated. The results are shown in Table 3.

TABLE 3

| | (Residual quantity %) | | | |
|---|---|---|---|---|
| | Active ingredient (% by weight) | | | |
| Solvent | BNDAP 10 (w/w %) | DCDT 2 (w/w %) | BNDFP 10 (w/w %) | DCDT 2 (w/w %) |
| PC | 100 | 100 | 100 | 100 |
| MBA | 95 | 100 | 90 | 100 |
| MDG | 49 | 100 | 41 | 100 |
| DMF | 99 | 100 | 95 | 100 |
| DEG | 13 | 98 | 10 | 97 |

PC: Propylene carbonate
MBA: 3-Methoxybutyl acetate
MDG: Diethylene glycol monomethyl ether
DMF: Diemethylformamide
DEG: Diethylene glycol

EXAMPLE

In a certain paper mill, the number of viable bacteria in white water in linerboard machine (production 200 tons/ day) was $10^7$/ml and a large quantity of slime was found thereby pinholes were formed on the paper products.

An one-pack liquid preparation of 15 wt % of BNDAP, 3 wt % of DCDT, 70 wt % of propylene carbonate and 12 wt % of diethylene glycol monomethyl ether was added to the stuff box part for each ply three times a day, each time for 1 hours, at a level of 47 ppm based on the pulp slurry. As a result, the number of viable bacteria decreased to $10^3$/ml and the quantity of slime greatly decreased and then the pinhole trouble could be solved.

The microbicidal/microbistatic compositions for industrial use and the industrial microbicidal/microbistatic method of the present invention exhibit excellent microbicidal/microbistatic effects and can accomplish intended microbicidal/microbistatic treatments with lower concentration of ingredients. Further, the microbicidal/microbistatic compositions of the present invention are also very useful because they are not affected their microbicidal and microbistatic power by temperature fluctuation (particular its decreasing).

What we claimed is:

1. A microbicidal/microbistatic composition for industrial use comprising
   (I) a nitrobromopropane derivative selected from the group consisting of:
      (a) 2-bromo-2-nitro-1,3-diacetyloxypropane, and
      (b) 2-bromo-2-nitro-1,3-diformyloxypropane; and
   (II) 4,5-dichloro-1,2-dithiol-3-one wherein (I) and (II) are present in a synergistic ratio of from 100:1 to 1:5 by weight.

2. The composition of claim 1 wherein (I) and (II) are present in the ratio of from 50:1 to 1:2 by weight.

3. The composition of claim 1 which is in the form of a one-pack liquid preparation together with an organic solvent and a dispersing agent comprising 50 parts by weight of (I) and (II), at least 0.01 parts by weight of the dispersing agent per part of the combined weight of I and II, the remainder being the hydrophilic organic solvent.

4. The composition of claim 3 wherein the organic solvent is a hydrophilic organic solvent selected from the group consisting of amides, glycols, glycol ethers, alcohols and esters.

5. The composition of claim 4 wherein the hydrophilic organic solvent is selected from the group consisting of dimethylformamide, methyl acetate, ethyl acetate, propyl acetate, 3-methoxybutyl acetate, 2-ethoxymethyl acetate, 2-ethoxyethyl acetate and propylene carbonate.

6. The composition of claim 3 wherein the organic solvent is a hydrophilic organic solvent selected from the group consisting of kerosene, heavy oil or spindle oil.

7. The composition of claim 3 in which the dispersing agent is a nonionic surfactant.

8. The composition of claim 1 which is in the form of an one-pack powdery preparation together with a solid diluent.

9. The composition of claim 8 in which the solid diluent is kaolin, clay, bentonite or carboxymethylcellulose.

10. A method of killing or inhibiting the growth of microorganisms comprising adding to an industrial medium
  (I) a nitrobromopropane derivative selected from the group consisting of:
    (a) 2-bromo-2-nitro-1,3-diacetyloxypropane, and
    (b) 2-bromo-2-nitro-1,3-diformyloxypropane; and
  (II) 4,5-dichloro,1,2-dithiol-3-one wherein (I) and (II) are present in a synergistic ratio of from 100:1 to 1:5 by weight, separately or simultaneously.

11. The method of claim 10 wherein (I) and (II) are present in a ratio of from 50:1 to 1:2 by weight.

12. The method of claim 10 wherein the total amount of (I) and (II) added to the industrial medium is 0.05 to 200 mg/l.

13. The method of claim 10 in which the industrial medium is papermaking process water, cooling water and washing water for various industries.

UNITED STATES PATENT AND TRADEMARK OFFICE
CERTIFICATE OF CORRECTION

PATENT NO. : 5,026,723

DATED : June 25, 1991

INVENTOR(S) : SAKAE KATAYAMA et al.

It is certified that error appears in the above-identified patent and that said Letters Patent is hereby corrected as shown below:

On the title page, item [73], add the following Assignee:
-- Yoshitomi Pharmaceutical Industries, Ltd., Japan --.

Cover Page [73]: See Assignment dated April 3, 1989, recorded April 14, 1989 at Real 5064, Frame 502. Add -- Yoshitomi Pharmaceutical Industries, Ltd., Japan -- as second Assignee.

Signed and Sealed this

Second Day of February, 1993

Attest:

STEPHEN G. KUNIN

*Attesting Officer*

*Acting Commissioner of Patents and Trademarks*